United States Patent
Naylor

(10) Patent No.: US 7,599,499 B2
(45) Date of Patent: Oct. 6, 2009

(54) METHOD FOR FITTING A HEARING AID TO THE NEEDS OF A HEARING AID USER AND ASSISTIVE TOOL FOR USE WHEN FITTING A HEARING AID TO A HEARING AID USER

(75) Inventor: Graham Naylor, Hellerup (DK)

(73) Assignee: Oticon A/S, Smørum (DK)

(*) Notice: Subject to any disclaimer, the term of this patent is extended or adjusted under 35 U.S.C. 154(b) by 869 days.

(21) Appl. No.: 10/491,010

(22) PCT Filed: Aug. 30, 2002

(86) PCT No.: PCT/DK02/00566

§ 371 (c)(1),
(2), (4) Date: Apr. 14, 2004

(87) PCT Pub. No.: WO03/030586

PCT Pub. Date: Apr. 10, 2003

(65) Prior Publication Data

US 2004/0264719 A1    Dec. 30, 2004

(30) Foreign Application Priority Data

Sep. 28, 2001  (DK) .............................. 2001 01426

(51) Int. Cl.
*H04R 29/00*     (2006.01)
(52) U.S. Cl. ..................... 381/60; 381/312; 600/559

(58) Field of Classification Search .................. 381/60, 381/58, 312–321, 328, 330, 23.1; 600/559; 73/585; 607/57
See application file for complete search history.

(56) References Cited

U.S. PATENT DOCUMENTS

| 3,645,354 | A | * | 2/1972 | Kliewer ....................... 181/129 |
| 6,110,126 | A | * | 8/2000 | Zoth et al. ................... 600/559 |
| 6,175,635 | B1 | * | 1/2001 | Meyer et al. ................. 381/314 |
| 6,574,342 | B1 | * | 6/2003 | Davis et al. .................. 381/314 |
| 6,882,732 | B2 | * | 4/2005 | Pavlakos ....................... 381/60 |
| 6,970,570 | B2 | * | 11/2005 | Goldstein .................... 381/321 |
| 2004/0101146 | A1 | * | 5/2004 | Laitinen et al. ............... 381/77 |

FOREIGN PATENT DOCUMENTS

EP          0695107        5/1996
WO     WO 00/52604   *  8/2000

* cited by examiner

*Primary Examiner*—Vivian Chin
*Assistant Examiner*—Lun-See Lao
(74) *Attorney, Agent, or Firm*—Dykema Gossett PLLC

(57) ABSTRACT

A method for prescribing the initial setting of signal processing parameters in a hearing aid to the needs of a hearing aid user includes gathering and storing in electronic form a first set of data concerning the user's audiological function and gathering and storing in electronic form a second set of data indicating the level of cognitive function possessed by the user. The two sets of data are used in combination for computing at least one suggested initial setting of the signal processing parameters of the hearing aid.

10 Claims, 3 Drawing Sheets

METHOD FOR FITTING A HEARING AID TO THE NEEDS OF A HEARING AID USER AND ASSISTIVE TOOL FOR USE WHEN FITTING A HEARING AID TO A HEARING AID USER

AREA OF THE INVENTION

The invention relates to a method and a tool for fitting a hearing aid to the needs of the hearing aid user. Such methods and tools usually comprise a computer with a computer-program or similar device, where the device has display means for visual display of data, data entry means for entering data into the device, data storing means, computation means for combining the input data, and data output means for outputting programming data to the hearing aid.

BACKGROUND OF THE INVENTION

When a hearing-impaired person seeks help in the form of a hearing aid, a process of evaluation, prescription, initial fitting and subsequent fine-tuning takes place, at the end of which it is hoped that the client is experiencing an optimal degree of benefit from the hearing aid concomitant with his/her personal circumstances (degree and type of hearing loss, listening needs, disposable income, etc.). Achievement of optimal benefit from a hearing aid fitting is dependent on many factors, not least of which is prescription of appropriate sound signal processing parameters according to which the hearing aid shall operate. Correct prescription of these parameters minimizes the need for subsequent fine-tuning adjustments and ensures that such fine-tuning as is necessary proceeds from a meaningful starting point.

It has long been accepted that different users are best served with different choices of sound signal processing in their hearing aids. First and foremost, the user's audiometric data (e.g. absolute threshold of hearing at various frequencies) are often used as input data to a procedure whereby appropriate choices of frequency response and compression parameters are prescribed. Additional diagnostic data which sometimes are utilised by such procedures define other aspects of the client's hearing loss, for example whether it is conductive or sensorineural in origin. Software modules used during the dispensing of hearing aids often contain such procedures in automated form.

It has also long been accepted that certain non-medical characteristics of the client should be considered when making choices concerned with which product features to include in the aid being dispensed. For example, clients with poor dexterity may do better with a hearing aid in which a user-operated volume control is superfluous.

The state of the art of prescribing appropriate signal processing in hearing aids is summarised in FIG. 1. Personal data in the optional categories of audiometry, audiological and otorhinolaryngological diagnosis, listening needs, special physical requirements serve as input to a decision-making process (manual or automatic) which contains rules for combining and processing the input data, and whose output is one or more recommendations about the signal processing characteristics to be implemented in the client's hearing aid.

It is known that people experience a reduction of cognitive capacity with age, which is thought to be due to the general effects of aging on the neurophysiological systems of the body. Cognitive deficits of this sort lead to poorer and slower performance in tasks requiring the interpretation and assimilation of information arriving from the environment. Included among such tasks is the understanding of speech. Recently it has been found that the optimum choice of signal processing in a hearing aid is not only dependent on the auditory characteristics of the client, but also on non-auditory characteristics, specifically the degree of generalised age-related reduction in cognitive capacity. Chronological age is not a perfect predictor of a person's level of cognitive function, but can be used as a simple indicator of high vs. low cognitive function, which is very reliable for the young and very old, and less reliable for people between about 60 and 80 years of age.

There are many medical conditions which are characterized by abnormal cognitive function in the sufferer, for example, Alzheimer's disease, dyslexia, schizophrenia, substance dependency, epilepsy. Although the causes of the abnormality differ widely, the effect in many cases is a general lowering of information-processing abilities similar to that seen with normal aging. A sub-group of conditions is characterized by abnormalities highly specific to the language processing or attention needed for effective speech understanding, for example, specific language impairment (SLI), central auditory processing deficit (CAPD). Thus, it is possible to use information about medical conditions other than hearing loss suffered by a hearing aid client to improve the decision-making process leading to recommendations affecting the signal processing to be implemented in the hearing aid.

It is also possible to identify categories of people whose cognitive processing capacity is likely to be unusually high, and thus make improved signal processing recommendations for these clients too. Such clients are typically characterised by having jobs which in themselves demand very high levels of cognitive processing, for example air traffic controllers, simultaneous interpreters, pilots.

SUMMARY OF THE INVENTION

One aspect of the invention concerns a method for prescribing the initial setting of signal processing parameters in a hearing aid to the needs of a hearing aid user. According to this aspect a first set of data concerning the user's audiological function are gathered and stored in electronic form and a second set of data indicating the level of cognitive function possessed by the user are gathered and stored in electronic form. The two sets of data are used in combination for computing at least one suggested initial setting of the signal processing parameters of a hearing aid.

By including the cognitive function believed to be possessed by the user, it is possible to suggest an initial setting which is more likely to fit the user's needs. Also, by the use of the method, the dispenser who is selling the hearing aid will automatically take this aspect of the client into account.

In an embodiment of the invention a third set of data which indicates at least one of the following:

the degree of variety in the user's lifestyle, frequency and importance of various sound environments, and previous hearing aid experience are gathered and stored in electronic form and used in combination with the two first sets of data for computing at least one suggested initial setting of the signal processing parameters of a hearing aid.

The user's lifestyle is important, as it indicates what kind of demands his or her hearing aid must meet, and the frequency and importance of various sound environments are also important as they indicate for instance whether large variations in the auditory environment are likely to be a part of a given user's lifestyle, and these factors have important bearing on the choice of the prescribed setting. Also, previous hearing aid experience is of importance when prescribing the initial setting of the hearing aid, as the amount of amplification giving optimally intelligible reproduction of speech is often more than can be tolerated by a user unaccustomed to the loudness of sounds provided by hearing aids. Thus, users without previous experience of hearing aid use are often better served by an initial setting with gain, frequency response and compression parameters adjusted for more comfortable but less clear reproduction of speech.

In a further embodiment of the method according to the invention the data indicating the level of cognitive function possessed by the user are derived from one or more of the following information sources: the user's age, the user's medical records, the user's present or previous occupation, a performance test designed to measure cognitive function, information derived from conversation with the user or persons associated with the user.

Preferably, the parameters to be set in the hearing aid include one or more of the following: gain, frequency response, compression ratio, compression time constants and volume control action.

According to a preferred embodiment of the method the audiometric data of the user are used to determine whether a rationale comprising wide dynamic range compression (WDRC) is indicated, and when a rationale comprising WDRC is indicated, an initial setting using compression release time constants below 400 milliseconds is prescribed for users with cognitive skills at or above average, and an initial setting using compression release time constants above 400 milliseconds is prescribed for users with cognitive skills below average.

If the WDRC is two channel different time constants for the low frequency and the high frequency areas can be set. The cross over frequency between the low and high frequency channel is set to 1,500 Hz. This is a commonly chosen cross over frequency, but it can be varied in a wide range without departing from the invention.

The release time constants in the WDRC are not to be set too short, as this may cause signal distortion. For people with cognitive skills at or above average, it is suggested according to the invention that the release time constant in the low frequency range is set between 40 and 100 milliseconds and in the high frequency range is set between 40 and 400 milliseconds.

The release time constants should not be too long, as this may result in the loss of too much speech information. For people with cognitive skills below average it is suggested that the release time constant in the high and the low frequency range are set between 400 and 1200 milliseconds.

In a preferred embodiment of the invention the following time constants are employed for individuals having cognitive function at or above average: Low frequency channel: release time of 80 milliseconds, and High frequency channel: release time of 320 milliseconds. For individuals having cognitive functions below average the following time constants are employed: Low frequency channel release time of 640 milliseconds and High frequency channel release time of 640 milliseconds. In all cases it is preferred to have an attack time of 20 milliseconds for both high and low frequency channels.

In a further preferred embodiment of the invention the performance capabilities of a number of different hearing aids are stored in electronic form, and the preferred initial setting is used for choosing amongst the different hearing aids the or those hearing aids in which said setting may be realized. The preferred setting may not be realizable in all variants of hearing aids and therefore the preferred setting may help in choosing the right hearing aid for the client.

In another embodiment a hearing aid is initially chosen for the client, and a set of data concerning this hearing aid and its performance capabilities are gathered and stored in electronic form, and said data set is used in combination with the two first data sets to generate a suggested initial setting, which can be realized within this hearing aid.

The invention also comprises an assistive tool for prescribing the initial setting of signal processing parameters in a programmable hearing aid to the needs of a hearing aid user.

This tool comprises:

means for storing data in electronic form concerning the hearing loss of the hearing aid user, and means for storing data in electronic form indicating the level of cognitive function possessed by the user, whereby the assistive tool further comprises means for combining the stored electronic data in order to generate at least one suggested initial setting of the signal processing parameters of the hearing aid.

In a preferred embodiment, the assistive tool comprises means for storing a further set of data in electronic form, which indicates at least one of the following:

the user's lifestyle, frequency and importance of various sound environments or, previous hearing aid experience, and further the assistive tool comprises means for combining the further set of stored electronic data with the previously stored data in order to generate at least one suggested initial setting of the signal processing parameters of the hearing aid.

The assistive tool may be used for correctly choosing a hearing aid for the client, or the hearing aid may be chosen in advance, and the assistive tool then incorporates data concerning the chosen hearing aid, and suggests the best initial setting which may be realized within the limitations of this hearing aid.

DESCRIPTION OF A PREFERRED EMBODIMENT

Figure 1:
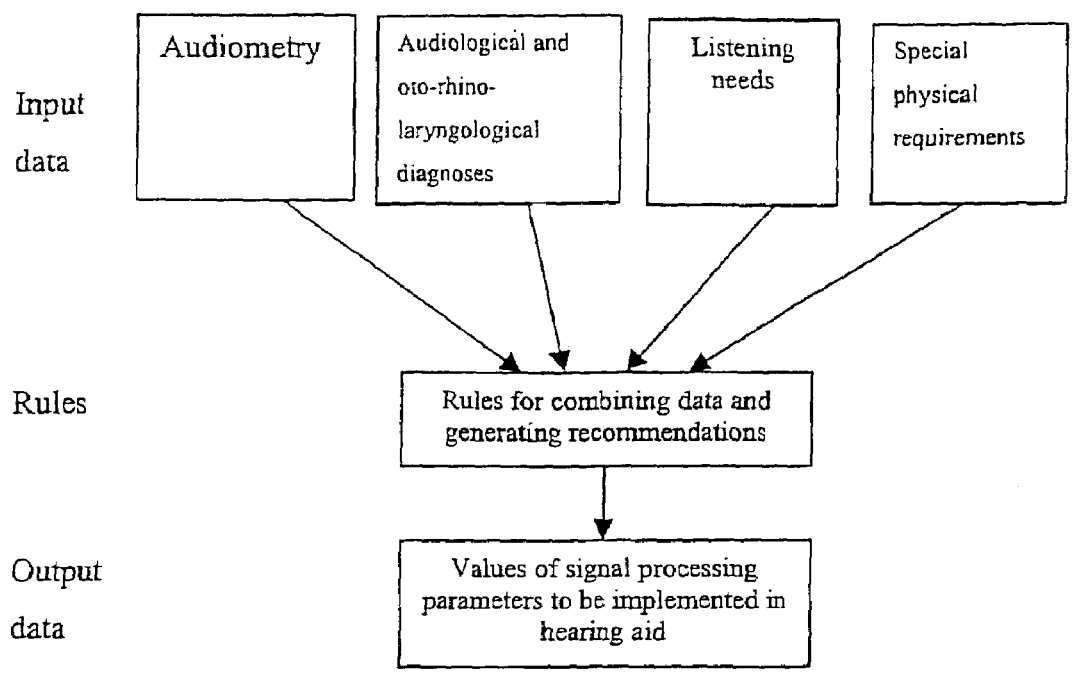
FIG. 1 shows in summarized form the state of the art of prescribing appropriate signal processing in hearing aids.

In FIG. 1 the usual fitting practice is schematically shown. As input to the fitting process the following sets of data are used: Audiometry; Audiological and oto-rhino-laryngological diagnoses, listening needs and special physical requirements. These sets of data are combined according to a given set of rules, and recommendations for the initial setting are generated as output data.

Figure 2:
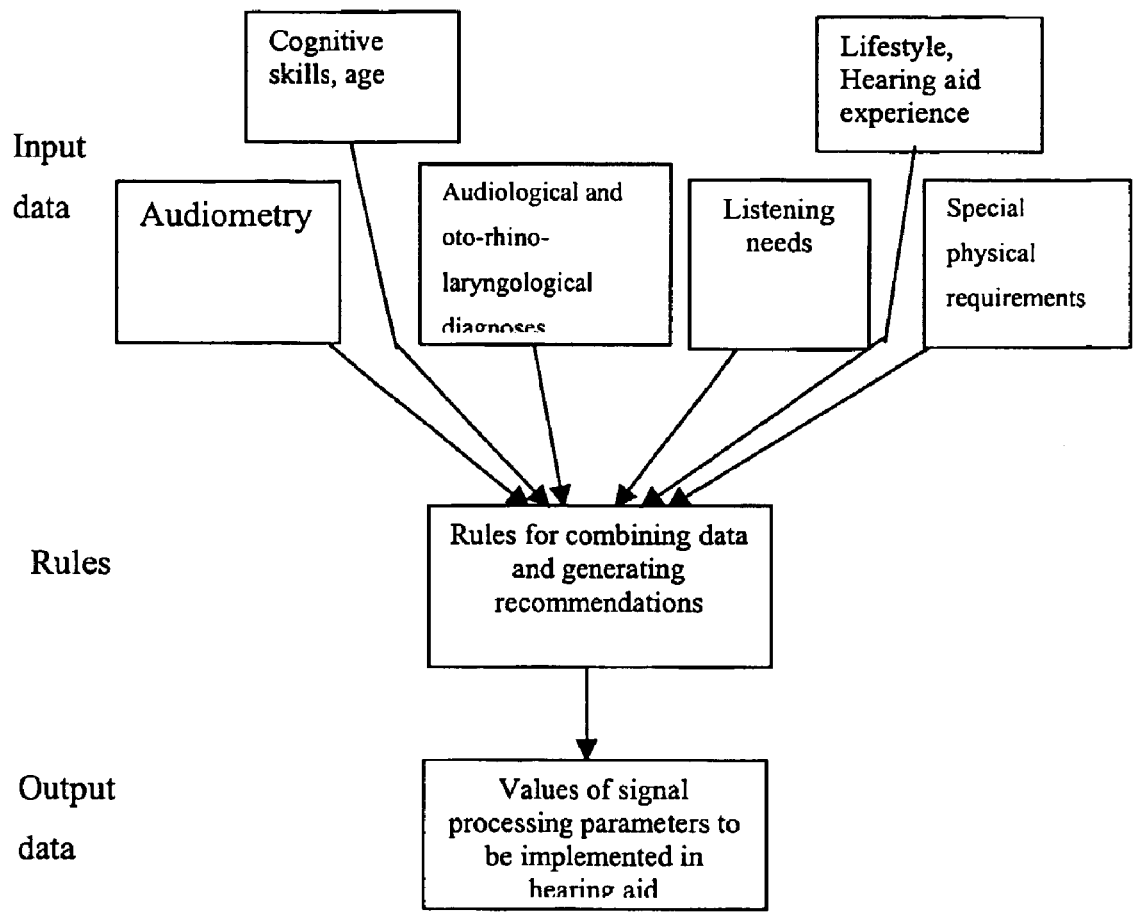
FIG. 2 shows in summarized form the prescription process according to the invention.

In FIG. 2 the fitting practice is shown when applying the new method according to the invention. As seen in the figure, the same data sets as in the prior art method are used as input along with a number of further data sets. The further data sets relate to the client's cognitive skills, age, lifestyle and hearing aid experience. The cognitive skills may be derived from the age information, or they may be derived from other sources. These other sources could be the client's medical record, the client's prior or present job activities, information derived from conversation with the client or persons relating to the client or it could be a test designed to display the extent of the client's cognitive skills.

Figure 3:
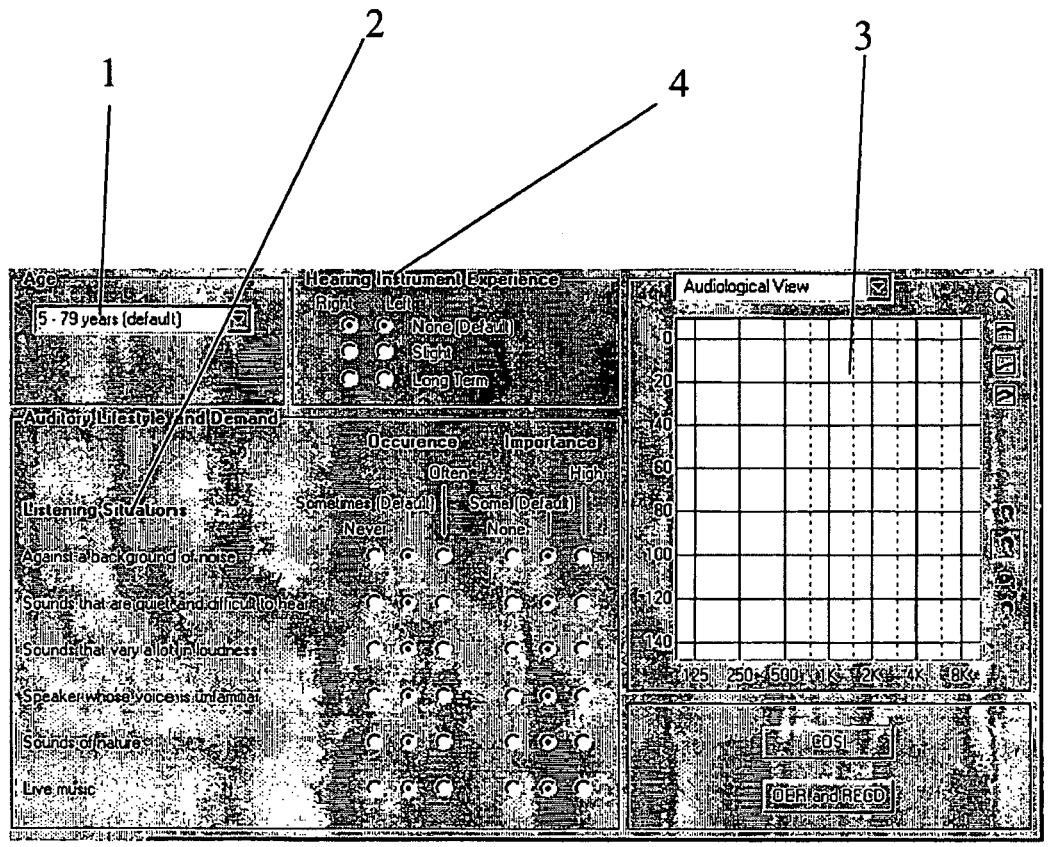
FIG. 3 shows the data fields for entering the data regarding lifestyle and cognitive function.

FIG. 3 is an example of the data input module for reception of data concerning the hearing aid user's age and lifestyle. In the "Age" field 1 in the top left corner information concerning the age of the client may be given, and the assistive tool will use this information as described in the following.

Below in the "Auditory Lifestyle and Demand" (ALD) window 2 a number of listening situations are listed, and the user is to state how often ("Occurrence") and how important ("Importance") the listening situation is. For each listening situation the user is to specify whether it occurs Often, Sometimes or Never and importance is also divided into three categories: High, Some and None. These Auditory Lifestyle and Demand data are indications of the user's level of activity. These data are used to generate scores relating to the lifestyle of the client in terms of outgoing extrovert lifestyle or quieter lifestyle. Also the "Hearing Instrument Experience" window 4 at the upper right corner is part of a given user's profile and has a bearing on the choice of initial setting.

The audiometric or hearing loss data of the user are loaded into the program in the usual way, and this is not further described. These data are displayed at the window 3.

In order to prescribe a setting for the hearing aid a rationale must be chosen. The rationale is a set of rules, which uses the audiometric data as input, and as output delivers a setting of the hearing aid's signal processing parameters. Different rationales will lead to different settings of the hearing aid for the same audiometric data. In the present case the audiometric data are used in a first step to generate probability factors or scores, which are assigned to each of a number of possible different rationales. The score indicates to what extent a given rationale is likely to provide a suitable fitting for the user.

The probability factors are then corrected in two further steps, a second step taking into account the ALD data and a third step taking into account the age of the user.

In the following we assume that three different rationales are available:

a) rationale with WDRC and with the following attack/release times:
  Low frequency channel: attack time=20 milliseconds, release time=80 milliseconds and
  High frequency channel: attack time=20 milliseconds, release time=320 milliseconds;

b) rationale with WDRC and with the following attack/release times:
  Low frequency channel: attack time=20 milliseconds, release time=640 milliseconds and
  High frequency channel: attack time=20 milliseconds, release time=640 milliseconds and c) rationale with linear amplification (no compressor)

We assume that the three rationales get assigned the same probability factor values or scores based on the audiometric data. In the second step the ALD data are taken into account, and if the ALD data suggests that the client has a dynamic and outgoing lifestyle with many variations in the auditory environment during the day, the two rationales with the WDRC will be assigned a higher correction value than the rationale using linear amplification. Thereby the rationales with the WDRC compressor have a higher score than the rationale using the linear amplification when the ALD data are taken into account.

In the third step the client's age is taken into account. Assume that the two rationales using the WDRC compressors have the same score based on audiometric and ALD data. If the client's age is above 80 years, the rationale using the WDRC compressor with slow release times (LF channel: release time=640 milliseconds; HF channel: release time=640 milliseconds) will be assigned a positive correction score and this rationale will end up with the highest score. If on the other hand, the client's age is below 60 years, the rationale using the WDRC compressor with the fast release times (LF channel: release time=80 milliseconds; HF channel: release time 320 milliseconds) will be assigned a positive score correction value and this rationale will end up with the highest score. In the age group from 60 to 80 the score is only slightly biased in the age-correction step.

Studies have shown that age and cognitive function to some extent are linked, and thus the age information can be used as an indicator of cognitive function. As mentioned above other indicators of the cognitive function possessed by the user may be used, such as medical journal, occupation or a test. It would be easy to modify the above described example of an input interface to encompass such data.

The age and release times suggested here are only examples, and they could be modified in many ways without departing from the general idea of the invention.

The invention claimed is:

1. A method for prescribing an initial setting of signal processing parameters in a hearing aid to the needs of a hearing aid user, comprising the steps of:
  gathering and storing in electronic form by a computer a first set of data concerning the user's audiological function,
  gathering and storing in electronic form by the computer a second set of data indicating the level of cognitive function possessed by the user, said data being selected from the group consisting of the user's age, the user's medical records, the user's present or previous occupation, a performance test designed to measure cognitive function, and information derived from conversation with the user or persons associated with the user, and
  computing by the computer from a combination of said first and second sets of data at least one suggested initial setting of signal processing parameters of the hearing aid, said signal processing parameters being selected from the group consisting of gain, frequency response, compression ratio, compression time constants and volume control action, and
  wherein the audiometric data of the user are used to determine whether a rationale which uses WDRC is suggested, and when a rationale comprising WDRC is prescribed, an initial setting having compression release time constants below 400 milliseconds are suggested for users with cognitive skills at or above average, and a prescribed initial setting using compression release time constants above 400 milliseconds are suggested for users with cognitive skills below average.

2. The method as claimed in claim 1, including gathering and storing in electronic form by the computer a third set of data which indicates at least one of the following: the user's lifestyle, frequency and importance of various sound environments and previous hearing aid experience, and using said third set of data in combination with the two first sets of data for computing at least one suggested initial setting of the signal processing parameters of a hearing aid.

3. The method as claimed in claim 1, comprising storing in electronic form performance capabilities of a number of different hearing aids, and using a preferred initial setting for choosing amongst the different hearing aids the or those hearing aids in which said setting may be realized.

4. The method as claimed in claim 1, wherein a set of data concerning the type of hearing aid and the performance capability of the hearing aid to be used by the user are gathered and stored in electronic form, and wherein said data set is used in combination with the two first data sets to generate a suggested initial setting, which can be realized within the hearing aid to be used by the user.

5. An assistive tool for prescribing an initial setting of signal processing parameters in a hearing aid to the needs of a hearing aid user, whereby the tool comprises: means for storing a first set of data in electronic form concerning the hearing loss of the hearing aid user, and means for storing a second set of data in electronic form indicating the level of cognitive function possessed by the user, and whereby the assistive tool further comprises means for combining the stored first and second sets of electronic data in order to generate at least one suggested initial setting of the signal processing parameters of the hearing aid, and wherein the audiometric data of the user are used to determine whether a rationale which uses WDRC is suggested, and when a rationale comprising WDRC is prescribed, an initial setting having compression release time constants below 400 milliseconds are suggested for users with cognitive skills at or above average, and a prescribed initial setting using compression release time constants above 400 milliseconds are suggested for users with cognitive skills below average.

6. The assistive tool as claimed in claim 5, whereby the tool comprises means for storing a further set of data in electronic form which indicates at least one of the following:

the user's lifestyle, frequency and importance of various sound environments or previous hearing aid experience, and whereby the assistive tool further comprises means for combining the further set of stored electronic data with the previously stored data in order to generate at least one suggested initial setting of the signal processing parameters of a hearing aid.

7. The assistive tool as claimed in claim 5, wherein means are provided for receiving input data concerning one or more of the following: the user's age, the user's medical record, the user's present or previous occupation, a performance test designed to measure cognitive function or information derived from conversation with the user or persons associated with user.

8. The assistive tool as claimed in claim 5, wherein the tool has means for storing a set of data in electronic form concerning the type of hearing aid to be used by the user, and wherein the tool has means for combining said information in combination with the two first data sets to generate a suggested initial setting, which can be realized within the hearing aid to be used by the user.

9. The assistive tool as claimed in claim 5, wherein means are provided for storing in electronic form sets of data relating to the performance capabilities of a number of different hearing aids, and wherein means are provided for choosing the hearing aid best suited to realize the suggested initial setting.

10. The assistive tool as claimed in claim 5, wherein means are provided for storing in electronic form a set of data relating to the performance capability of a previous chosen hearing aid and where means are provided for combining the performance capability data with the previously stored data in order to generate an initial setting for the chosen hearing aid and where means are provided for displaying the initial setting.

* * * * *